United States Patent [19]
Airey et al.

[11] Patent Number: 5,288,731
[45] Date of Patent: Feb. 22, 1994

[54] 2,6-METHANO-2H-1-BENZOXOCINCARBOXYLIC ACIDS, ESTERS AND AMIDES

[75] Inventors: John E. Airey, King of Prussia; Matthew R. Powers, Barto; Walter Rodriguez, Douglasville, all of Pa.; Raymond D. Youssefyeh, Princeton Junction,, N.J.

[73] Assignee: Rhone-Poulenc Rorer Pharmaceuticals Inc., Collegeville, Pa.

[21] Appl. No.: 925,044

[22] Filed: Aug. 5, 1992

Related U.S. Application Data

[63] Continuation-in-part of Ser. No. 620,241, Nov. 29, 1990, abandoned, which is a continuation-in-part of Ser. No. 582,890, Oct. 1, 1990, abandoned, which is a continuation-in-part of Ser. No. 186,824, Apr. 27, 1988, Pat. No. 4,863,921.

[51] Int. Cl.$^5$ ................ A61K 31/55; C07D 453/02
[52] U.S. Cl. ............... 514/305; 514/224.2; 514/230.5; 514/299; 514/304; 514/320; 544/47; 544/105; 546/112; 546/126; 546/133; 546/196; 546/354; 546/355; 546/386
[58] Field of Search .......... 546/133; 514/305; 549/386

[56] References Cited

U.S. PATENT DOCUMENTS

| | | | |
|---|---|---|---|
| 3,869,475 | 3/1975 | Mechoulam et al. | 549/386 |
| 4,612,319 | 9/1986 | King | 514/305 |
| 4,857,517 | 8/1989 | Youssefyeh et al. | 514/161 |
| 4,859,683 | 8/1989 | Youssefyeh et al. | 514/299 |
| 4,863,921 | 9/1989 | Youssefyeh et al. | 514/230.5 |
| 4,910,193 | 3/1990 | Buchheit | 514/305 |
| 4,924,010 | 5/1990 | Youssefyeh et al. | 546/133 |
| 4,959,485 | 9/1990 | Youssefyeh et al. | 549/461 |

Primary Examiner—Glennon R. Hollrah
Assistant Examiner—Scott C. Rand
Attorney, Agent, or Firm—James A. Nicholson; Martin F. Savitzky; Raymond S. Parker, III

[57] ABSTRACT

Novel compounds which are 2,6-methano-2H-1-benzoxocincarboxamides having 5-HT$_3$-antagonist properties including unique CNS, antiemetic and gastric prokinetic activities and which are void of any significant D$_2$ receptor binding affinity, therapeutic compositions and methods of treatment of disorders which result from 5-HT$_3$ activity using said compounds. Processes for their preparation and the preparation of their intermediates are also disclosed.

16 Claims, No Drawings

2,6-METHANO-2H-1-BENZOXOCINCARBOXYLIC ACIDS, ESTERS AND AMIDES

This application is a continuation-in-part of application Ser. No. 07/620,241, now abandoned, which was filed Nov. 29, 1990, which is a continuation-in-part of application Ser. No. PCT/US89/01739 having an International Filing Date of Apr. 25, 1989, which designates the United States and which now has entered the U.S. National stage as application Ser. No. 07/582,890, now abandoned, which we filed Oct. 1, 1990, which, in turn, is a continuation-in-part of application Ser. No. 07/186,824, filed Apr. 27, 1988, which issued Sep. 5, 1989, as U.S. Pat. No. 4,863,921.

FIELD OF THE INVENTION

This invention relates to processes for the preparation, separation and purification of 2,6-methano-2H-1-benzoxocincarboxylates, 2,6-methano-2H-1-benzoxocincarboxylic acids and to amide compounds prepared from these acids which exhibit 5-HT$_3$-antagonist properties including unique CNS, antiemetic and gastric prokinetic activity which are void of any significant D2 receptor binding affinity.

5-Hydroxytryptamine, abbreviated "5-HT", is commonly known as serotonin. Serotonin is found throughout the body including the gastrointestinal tract, platelets, spleen and brain and appears to be involved in a great number of physiological processes such as neurotransmission at certain neurones in the brain, and is implicated in a number of central nervous system (CNS) disorders. Additionally, serotonin appears to act as a local hormone in the periphery; it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors has been proposed: D-receptors are 5-HT$_2$-receptors; M-receptors are termed 5-HT$_3$-receptors; and all other receptors, which are clearly not 5-HT$_2$ or 5-HT$_3$, have been referred to as 5-HT$_1$-like and work is being continued on this classification.

5-HT$_3$-receptors have been located in non-neurological tissue, brain tissue, and a number of peripheral tissues related to different responses. It has been reported that 5-HT$_3$-receptors are located on peripheral neurones where they are related to serotonin's (excitatory) depolarizing action. The following subtypes of 5-HT$_3$-receptor activity have been reported: action involving postganglionic sympathetic and parasympathetic neurones, leading to depolarization and release of noradrenaline and acetylcholine, respectively (5-HT$_{3B}$ subtype); action on enteric neurones, where serotonin may modulate the level of acetylcholine (5-HT$_{3C}$ subtype); and action on sensory nerves such as those involved in the stimulation of heart nerve endings to produce a reflex bradycardia (5-HT$_{3A}$ subtype), and also in the perception of pain.

Highly selective 5-HT$_3$-antagonists have been shown to be very effective at controlling and preventing emesis (vomiting) induced by chemotherapy and radiotherapy in cancer patients. The anti-emetic effects of 5-HT$_3$-antagonists in animals exposed to cancer chemotherapy or radiation are similar to those seen following abdominal vagotomy. The antagonist compounds are believed to act by blocking 5-HT$_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an reflex mechanism, thus providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific 5-HT$_3$-receptors on the primary afferent neurones.

5-HT$_3$-antagonists are also reported to exert potential antipsychotic effects, and are believed to be involved in anxiety. Although not understood well, the effect is believed to be related to the indirect blocking of serotonin 5-HT$_3$-mediated modulation of dopamine activity. Many workers are investigating various compounds having 5-HT$_3$-antagonist activity.

The development of 5-HT$_3$ agents originated from work carried out with metoclopramide (Beecham's Maxolon, A. H. Robins' Reglan), which is marketed for use in the treatment of nausea and vomiting at high doses. Metoclopramide is a dopamine antagonist with weak 5-HT$_3$-antagonist activity, which becomes more prominent at higher doses. It is reported that the 5-HT$_3$ activity and not the dopamine antagonism is primarily responsible for its antiemetic properties. Other workers are investigating this compound in connection with the pain and vomiting accompanying migraine.

Merrell Dow's compound MDL-72222 is reported to be effective as an acute therapy for migraine, but toxicity problems have reportedly ended work on this compound. Currently four compounds, A. H. Robins' Zacopride, Beecham's BRL-43694, Glaxo's GR-380-32F and Sandoz' ICS-205-930 are in clinical trials for use in chemotherapy-induced nausea and vomiting. GR-38032F is also in clinical trials in anxiety and schizophrenia, and reportedly, Zacopride in anxiety, while ICS-205-930 has been shown to be useful in treating carcinoid syndrome.

Compounds reported as gastroprokinetic agents include Beecham's BRL-24924, which is a serotonin-active agent for use in gut motility disorders such as gastric paresis, audition reflux esophagitis, and is known to have also 5-HT$_3$-antagonist activity.

Metoclopramide, Zacopride, Cisapride and BRL-24924 are characterized by a carboxamide moiety situated para to the amino group of 2-chloro-5-methoxy aniline. BRL-43694, ICS-205-930, GR-38032F and GR-65630 are characterized by a carbonyl group in the 3-position of indole or N-methyl indole. MDL-72222 is a bridged azabicyclic 2,4-dichlorobenzoate, while Zacopride, BRL-24924, BRL-43694 and ICS-205930 have also bridged azabicyclic groups in the form of a carboxamide or carboxylic ester.

Bicyclic oxygen containing carboxamide compounds wherein the carboxamide is ortho to the cyclic oxygen moiety are reported to have antiemetic and antipsychotic properties in EPO Publication No. 0234872.

Dibenzofurancarboxamides and 2-carboxamide-substituted benzoxepines are reported to have 5-HT$_3$-antagonist and gastroprokinetic activity in U.S. Pat. Nos. 4,859,683, 4,857,517, 4,924,010 and 4,863,921, all of which are assigned to the same assignee as the present application.

Among the reported compounds are stereoisomers which are synthesized by using chiral synthesis, i.e., asymmetric induction methods of synthesis.

REPORTED DEVELOPMENTS

U.S. Pat. No. 4,863,921, as mentioned above, discloses dibenzofurancarboxamides having 5-HT$_3$-antagonist properties. The synthesis of these dibenzofurans is described in the specification by first esterifying salicyclic acid and then reacting the phenol with 3-bromocyclohexene under basic conditions to obtain the phenyl cyclohexenyl ether. Claisen rearrangement at high temperature results in the methyl 3-(3'-cyclohexene)salicylate. Ring closure using trifluoroacetic acid results in formation of the 5a,6,7,8,9,9a-hexahydrodibenzofuran ring. This is then hydrolyzed to the acid with aqueous base and condensed with an amine of the formula H2N-Z to obtain the corresponding carboxamides of the invention. It has been reported that formation of these 5a,6,7,8,9,9a-hexahydrodibenzofuran compounds results in the formation of the cis and trans isomers. Further, certain of the compounds have at least one asymmetric carbon atom and as a result the racemic mixtures may consist of a number of diastereomers or enantiomers.

Various methods have been used to separate these isomers and are described in U.S. Pat. No. 4,863,921 and again in International Patent Application PCT/US89/01739 which has been published as International Publication Number: WO 89/10364. It has been described in these publications of the particular separation of 2-chloro-5a,6,7,8,9,9a-hexahydrodibenzofuran-4-(N-1-azabicyclo[2.2.2.]oct-3-yl)carboxamide into its cis and trans isomers and its eight stereoisomers. The separation of the intermediate reaction materials is also described.

According to the disclosures in U.S. Pat. No. 4,863,921 and PCT/US89/01739, ring closure of methyl 3-(3-hexenyl)-5-chlorosalicylate with trifluoroacetic acid results in methyl 2-chloro-cis-5a,6,7,8,9,9a-hexahydrodibenzofuran-4-carboxylate and 2-chloro-trans 5a,6,7,8,9,9a-hexahydrodibenzofuran-4-carboxylate. These esters are then hydrolyzed to the acids and separately reacted with 3-aminoquinuclidine to obtain the desired cis and trans carboxamide racemic mixtures.

SUMMARY OF THE INVENTION

We have unexpectedly found that when methyl 3-(3'-hexenyl)-5-chlorosalicylate is reacted with trifluoroacetic acid and/or sulfuric acid according to procedures of U.S. Pat. No. 4,863,921 and PCT/US89/01739, the ring closed products prepared are methyl 2-chloro-5a,6,7,8,9,9a-hexahydrodibenzofuran-4-carboxylate and methyl 8-chloro-2,6-methano-2H-3,4,5,6-tetrahydro-1-benzoxocin-10-carboxylate.

As a result, the products obtained upon hydrolysis of the ester to the acid followed by treatment with 3-aminoquinuclidine are 2-chloro-5a,6,7,8,9,9a-hexahydrodibenzofuran-4-(N-1-azabicyclo[2.2.2.]oct-3-yl)carboxamide and 10-[N azabicyclo[2.2.2.]octan-3-yl)carboxamido]-8-chloro-2,6-methano-2H-3,4,5,6,-tetrahydro-1-benzoxocine.

As a result of this unexpected discovery, the present invention comprises a new class of benzoxocincarboxylate, carboxylic acid and carboxamide compounds, exhibiting valuable pharmacological properties and prepared by the acidic cyclization of the compounds according to Formula A.

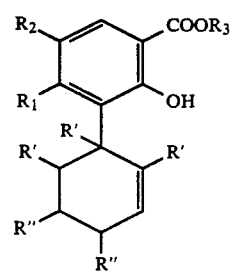

Formula A where R$_1$, R$_2$, R$_3$, R' and R" are as described below.

Generally, this invention comprises compounds having selective 5HT$_3$-antagonist properties, their use in the treatment of various gastric prokinetic disorders, pharmaceutical preparations and processes for their preparation and the preparation of their intermediates.

The compounds of this invention are described by Formula I:

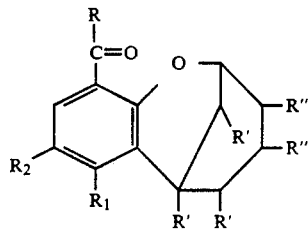

Formula I where:
R is OH, OR$_3$ or NH-Z;
R$_1$ is hydrogen or an amino or alkylamino optionally substituted with a protecting group, halo or haloalkyl;
R$_2$ is hydrogen, halo, sulfamyl, mono- and di-alkylsulfamyl optionally substituted with a protecting group or haloalkyl;
R$_3$ is alkyl;
R' and R" are hydrogen or alkyl: vicinal R' and/or R" groups may form a C=C double bond; and
Z is

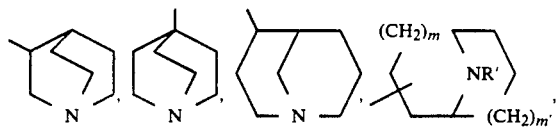

-continued

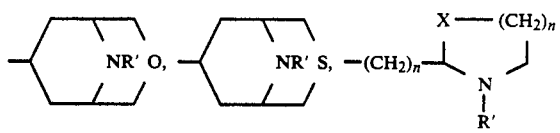

or

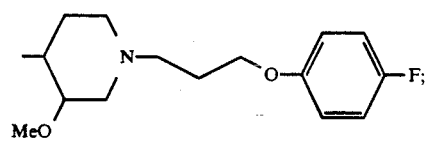

where m is 0-2, n is 1-2 and X is N or S; and its stereoisomers, enantiomers, diastereoisomers and racemic mixtures; or pharmaceutically acceptable salts thereof.

DETAILED DESCRIPTION OF THE INVENTION

As employed above and throughout the disclosure, the following terms, unless otherwise indicated, shall be understood to have the following meanings:

"Alkyl" means, either alone or within the various substituents, defined hereinbefore, a hydrocarbon having one to about 20 carbon atoms.

"Lower alkyl" means alkyl having one to about six carbon atoms, for example, methyl, ethyl, propyl, isopropyl, butyl, isobutyl, amyl and hexyl. Preferred lower alkyl includes methyl, ethyl and propyl.

"Halo" means Cl, Br, I and F. Preferred halo is Cl and Br, while preferred haloalkyl is trifluoromethyl.

"Protecting group" means that if it is necessary or desirable to prevent cross-reaction between chemically active substituents and an amino group, either during coupling reactions or at other points in the reaction sequence, the substituent or the amine may be protected by a standard blocking group which may be retained or subsequently removed, as required, by known methods to afford the desired product or precursor (see, for examole, Green, "Protective Groups in Organic Synthesis", Wiley, N.Y., 1981). The preferred protecting group is acyl.

"Acyl" means an organic radical derived from an organic acid, a carboxylic acid, by the removal of its acid hydroxy group. Preferred acyl groups are benzoyl and lower alkyl carboxylic acid groups such as acetyl and propionyl.

The following nomenclature is used in the description of this invention.

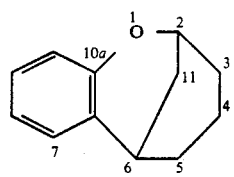

which is 2,6-methano-2H-3,4,5,6-tetrahydro-1-benzoxocine.

Preferred compounds of this invention include those compounds of Formulae II and III

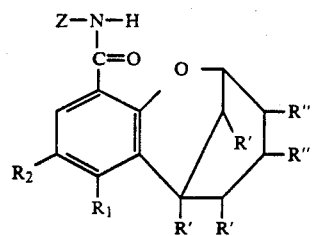
Formula II

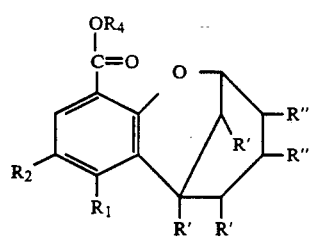
Formula III where:
$R_1$ is hydrogen, amino or alkylamino;
$R_2$ is hydrogen or halo; and
$R_4$ is H or alkyl;
Z is

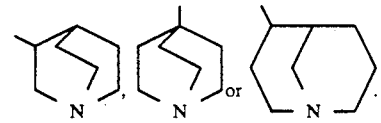

More preferred compounds include those of Formulae II and III where:
$R_1$ is amino or loweralkylamino and $R_2$ is hydrogen;
$R_1$ is hydrogen and $R_2$ is halo, or
$R_1$ is amino and $R_2$ is halo.
The most preferred compounds of Formulae II are described where:
$R_1$ is hydrogen or amino;
$R_2$ is chloro or bromo; and
Z is

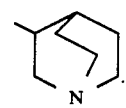

The most preferred compounds of Formulae III are described where:
$R_1$ is hydrogen or amino;
$R_2$ is chloro or bromo; and
$R_4$ is hydrogen or methyl;

The present compounds are prepared by the following general procedure.

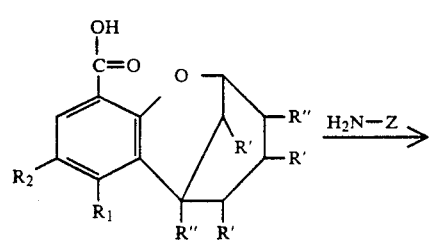

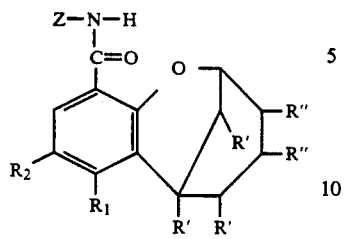

Condensation of a substituted 2,6-methano-2H-3,4,5,6-tetrahydro-1-benzoxocin-10-carboxylic acid, 2,6-methano-2H-3,4-dihydro-1-benzoxocin-10-carboxylic acid, 2,6-methano-2H-5,6-dihydro-1-benzoxocin-10-carboxylic acid, 2,6-methano-2,3,4,5-tetrahydro-1-benzoxocin-10-carboxylic acid or 2,6-methano-2H-1-benzoxocin carboxylic acid, their acid halides or esters with an amine of the formula $H_2N$-Z results in the corresponding carboxamide.

In general, this reaction is carried out at decreased temperatures, such as 0° C. by adding ethyl chloroformate to a reaction mixture of the acid in chloroform in the presence of triethylamine. This is then reacted with the amine of the formula $H_2N$-Z to obtain the desired product. Condensation may also be carried out in the presence of a dehydrating catalyst such as a carbodiimide in a solvent at normal temperatures.

The most preferred compounds are prepared by reacting the $R_1$ and $R_2$ substituted 2,6-methano-2H-3,4,5,6-tetrahydro-1-benzoxocin-10-carboxylic acids, acid halides or esters with 3-aminoquinuclidine to obtain $R_1$ and $R_2$ substituted 10-[N-(1-azabicyclo[2.2.2.]octan-3-yl)carboxamido]-2,6-methano-2H-3,4,5,6-tetrahydro-1-benzoxocines.

This reaction may take place with optically pure starting materials such as the acid or amine which have a specific configuration to obtain the desired stereospecific amide. Further, the amide may be formed as above and then separated by known techniques into the desired stereoisomers. Preparation and separation will be described in more detail later in this application.

The starting materials, that is the substituted 2,6-methano-2H-3,4,5,6-tetrahydro-1-benzoxocin-10-carboxylic acid, 2,6-methano-2H-3,4-dihydro-1-benzoxocin-10-carboxylic acid, 2,6-methano-2H-5,6-dihydro-1-benzoxocin-10-carboxylic acid, 2,6-methano-2,3,4,5-tetrahydro-1-benzoxocin-10-carboxylic acid and 2,6-methano-2H-1-benzoxocin-10-carboxylic acids are also novel. Their preparation will be described in more detail later.

The following reaction scheme was reported in U.S. Pat. No. 4,863,921 and PCTIUS89/01739:

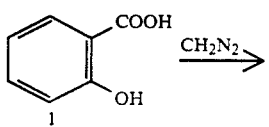

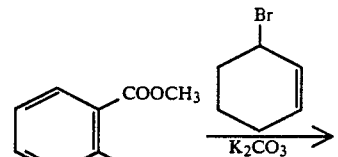

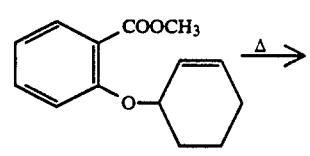

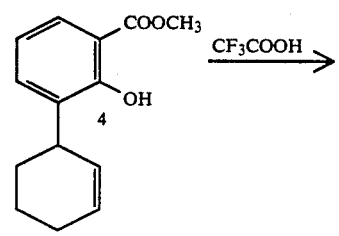

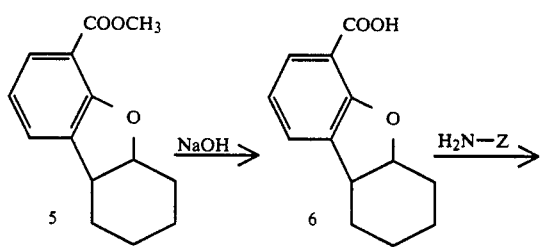

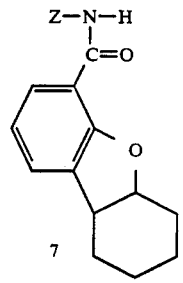

Salicyclic acid is first esterified and then the phenol(2) is treated with 3-bromocyclohexene under basic conditions in a polar medium to obtain the phenyl cyclohexenyl ether (3). Claisen rearrangement at high temperature results in the methyl 3-(3'-cyclohexene)-salicylate (4). Ring closure using trifluoroacetic acid results in the formation of the 5a,6,7,8,9,9a-hexahydrodibenzofuran ring (5). This is then be hydrolyzed to the acid (6) with aqueous base and then reacted with an amine of the formula $H_2N$-Z to obtain the desired dibenzofurancarboxamides (7).

It was also described in U.S. Pat. No. 4,863,921 and PCT/US89/01739 that the ring closure of methyl 3-(3'-cyclohexene)salicylate resulted in the formation of cis and trans isomers of the dibenzofuran acid. These acid intermediates were then either resolved or used as the racemic mixtures and then reacted with the resolved or unresolved amine to obtain the final amide products.

In one specific instance 2-chloro-5a,6,7,8,9,9a-hexahydrodibenzofuran-4-[N-(1-azabicyclo[2.2.2]octan-3- yl)carboxamide hydrochloride which has three asymmetric centers was prepared by condensation of racemic 2-chloro-5a,6,7,8,9,9a-hexahydrodibenzofuran-4-carboxylic acid and racemic 3-aminoquinuclidine. The resultant racemic mixture was known to contain eight individual stereoisomers. This consisted of four cis isomers and four trans isomers. One of the tasks of the present inventors was to separate each of the eight isomers and determine its specific configuration as well as its chemical, physical and pharmacological properties. In the course of this work a new series of compounds was isolated from the above racemic mixture. These were studied, characterized and found to be stereoisomers of 10-[N-(1-azabicyclo-[2.2.2.]octan-3-yl)carboxamido]-8-chloro-cis-2,6-methano-2H-3,4,5,6-tetrahydro-1-benzoxocine

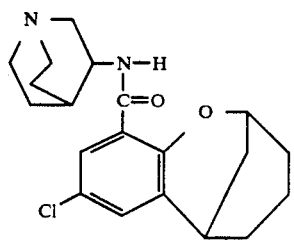

In developing the source of these novel benzoxocines the ring closure of 3-(3-cyclohexenyl)-5-chlorosalicylate with trifluoroacetic acid and/or with sulfuric acid was studied.

Example 24 of U.S. Pat. No. 4,863,921 and PCT/US89/01739, which is described in detail at the end of the examples of this application, describes the preparation of methyl 2-chloro-cis-5a,6,7,8,9,9a-hexahydrodibenzofuran-4-carboxylate and methyl 2-chloro-trans-5a,6,7,8,9,9a-hexahydrodibenzofuran-4-carboxylate. After the ring closure with trifluoroacetic acid the mixture was chromatographed into four fractions to separate the isomers. The first fraction was stated to be a mixture of at least two materials. The second fraction was stated to be the cis isomer. The third fraction was stated to be a mixture of cis and trans isomers. The fourth fraction was stated to be the trans isomer.

The present inventors, with the aid of X-ray crystallography determined that the second fraction was indeed methyl 2-chloro-cis-5a,6,7,8,9,9a-hexahydrodibenzofuran-4-carboxylate. However, it was unexpectedly found that the fourth fraction was not 2-chloro-trans-5a,6,7,8,9,9a-hexahydrodibenzofuran-4-carboxylate but rather 8-chloro-cis-2,6-methano-2H-3,4,5,6-tetrahydro-1-benzoxocin-10-carboxylate. Therefore, when the material from the fourth fraction was hydrolyzed according to Example 26 of U.S. Pat. No. 4,863,921 and PCT/US89/01739 and then condensed with 3-aminoquinuclidine according to Example 27 of the same references, the 10-[N-(1-azabicyclo-2.2.2.]octan-3-yl)carboxamido]-8-chloro-cis-2,6-methano-2H-3,4,5,6-tetrahydro-1-benzoxocine was prepared and not 2-chloro-trans-5a,6,7,8,9,9a-hexahydrodibenzofuran-4-[N-(1-azabicyclo[2.2.2.]octan-3-yl)carboxamide as had been been reported.

As a result, the compounds of Formula I were developed which are a novel class of benzoxocincarboxylic acids, esters and amides. The benzoxocincarboxamides were found to unexpectedly exhibit valuable pharmacological properties as 5-$HT_3$-antagonists. This will be described in further detail later.

The starting materials of this invention are prepared by the following reaction scheme:

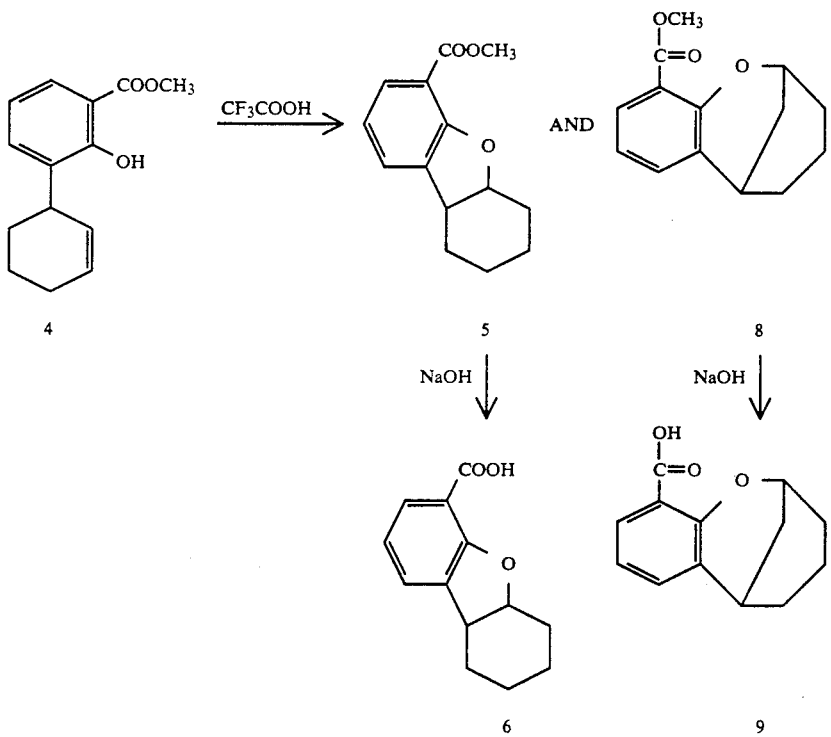

Ring closure of methyl 3-(3'-cyclohexene)salicylate (4) results in the formation of the dibenzofuran (5) and 2,6-methano-2H-3,4,5,6-tetrahydro-1-benzoxocine (8) esters. These may be separated at this stage and resolved or the mixed esters are hydrolyzed to the acids (6 and 9), separated and resolved.

Ring closure with trifluoroacetic gives 3:1 dibenzofuran to benzoxocine while the use of conc. sulfuric acid results in formation of predominately the 2,6-methano-2H-3,4,5,6-tetrahydro-1-benzoxocine. Trifluoroacetic acid in combination with sulfuric acid gives varying amounts of dibenzofuran to benzoxocine depending on the amounts of each acid present.

The process for the preparation of substantially optically pure benzoxocines which do not racemize is disclosed in a copending application U.S. Ser. No. 07/620,240, filed on the same date as this application.

Preparation of the 2,6-methano-2H-1-benzoxocine and its dihydro derivatives may be synthesized by the following reaction schemes:

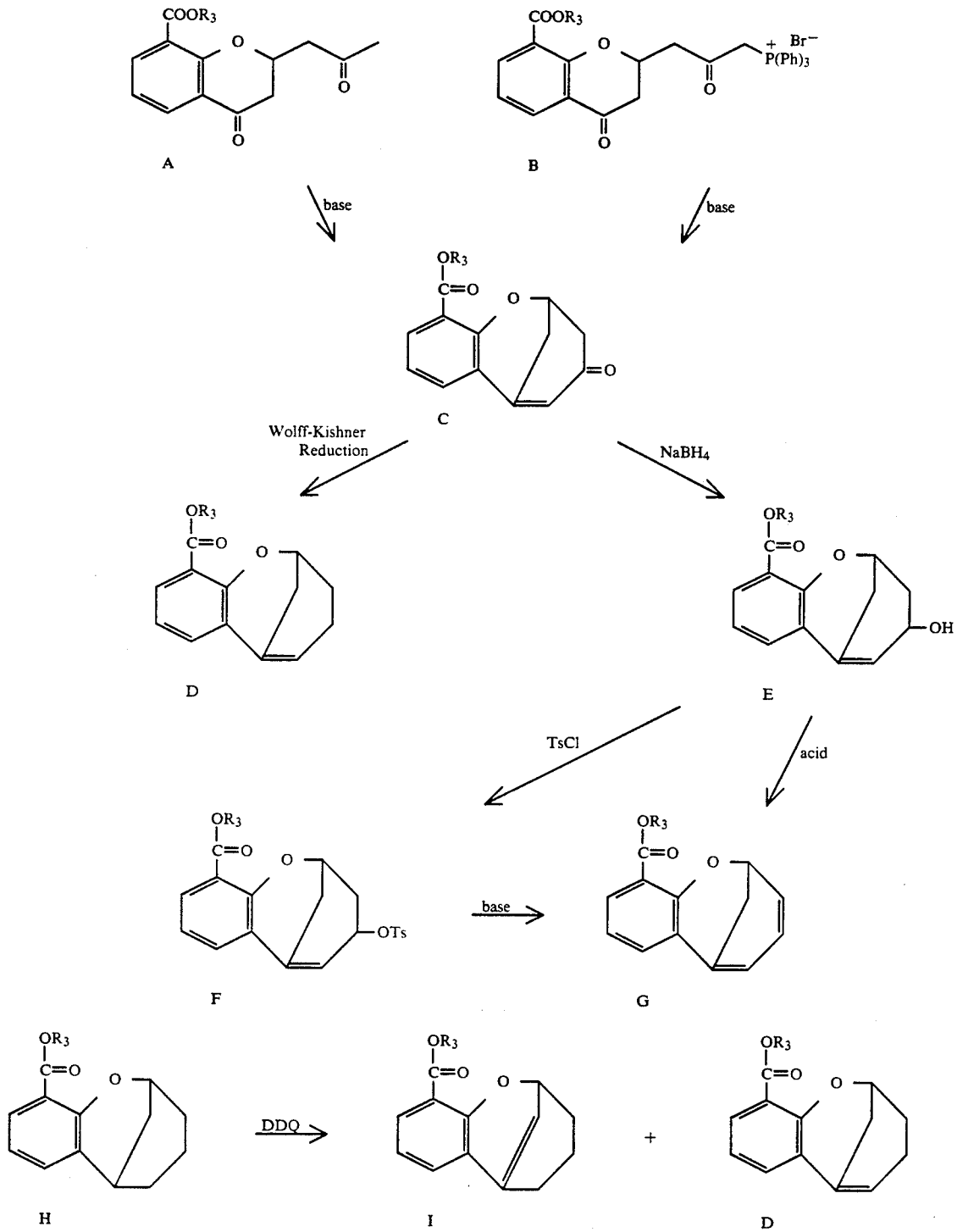

Treatment of the dihydrochromone (A) with strong base such as potassium t-butoxide ring closes to obtain the dihydrobenzoxocine ketone (C). This may also be prepared from the triphenylphosphonate (B). Wolff-Kishner reduction of the ketone compound (C) with hydrazine to form the hydrazide followed by reduction with potassium hydroxide results in 2,6-methano-2H-3,4-dihydro-1-benzoxocin-10-carboxylate (D).

When the dihydrobenzoxocine ketone (C) is subjected to sodium borohydride reduction followed by treatment of the alcohol (E) with acid the 2,6-methano-2H-1-benzoxocin-10-carboxylate (G) results. Treatment of the alcohol (E) with tosylchloride followed by strong base such as sodium methoxide also gives the carboxylate (G).

When 2,6-methano-2H-3,4,5,6-tetrahydro-1-benzoxocin-10-carboxylate is reacted with DDQ, 2,3-dichloro-5,6-dicyano-1,4-benzoquinone, the mixed dihydrobenzoxocin-10-carboxylate compounds (I) and (D) result. These can then be separated by chromatographic methods.

When $R_2$ substitution is desired, the above reactions are carried out starting with the proper 5-substituted salicyclic acid. Thus the following reaction sequences take place When $R_2$ substitution is halo, the above reaction sequence is carried out starting with 5-halo salicyclic acid.

In the case where $R_2$ is sulfamyl, it is best that this group be protected initially with an acetyl group or the like and then deacetylated.

When $R_1$ is an amine function this also should be protected with a protecting group, preferably an acetyl group and then deacetylated after the benzoxocine ring system has been formed.

Treatment of a 4-amino or 4-alkylamino salicyclic acid with MeOH/HCl followed by acetylation with acetyl chloride in pyridine in the usual manner results in the 4-acetylamino or 4-acetylalkylaminosalicylates. Demethylation of the alcohol and ester is then carried out using boron tribromide in a non polar solvent to obtain the 4-acetylamino or 4-acetylalkylaminosalicyclic acids. Esterification is accomplished with diazomethane as before and the resultant ester is used in a similar manner as above to obtain the desired 1-amino or alkylamino benzoxocin 10-carboxylic acid compounds.

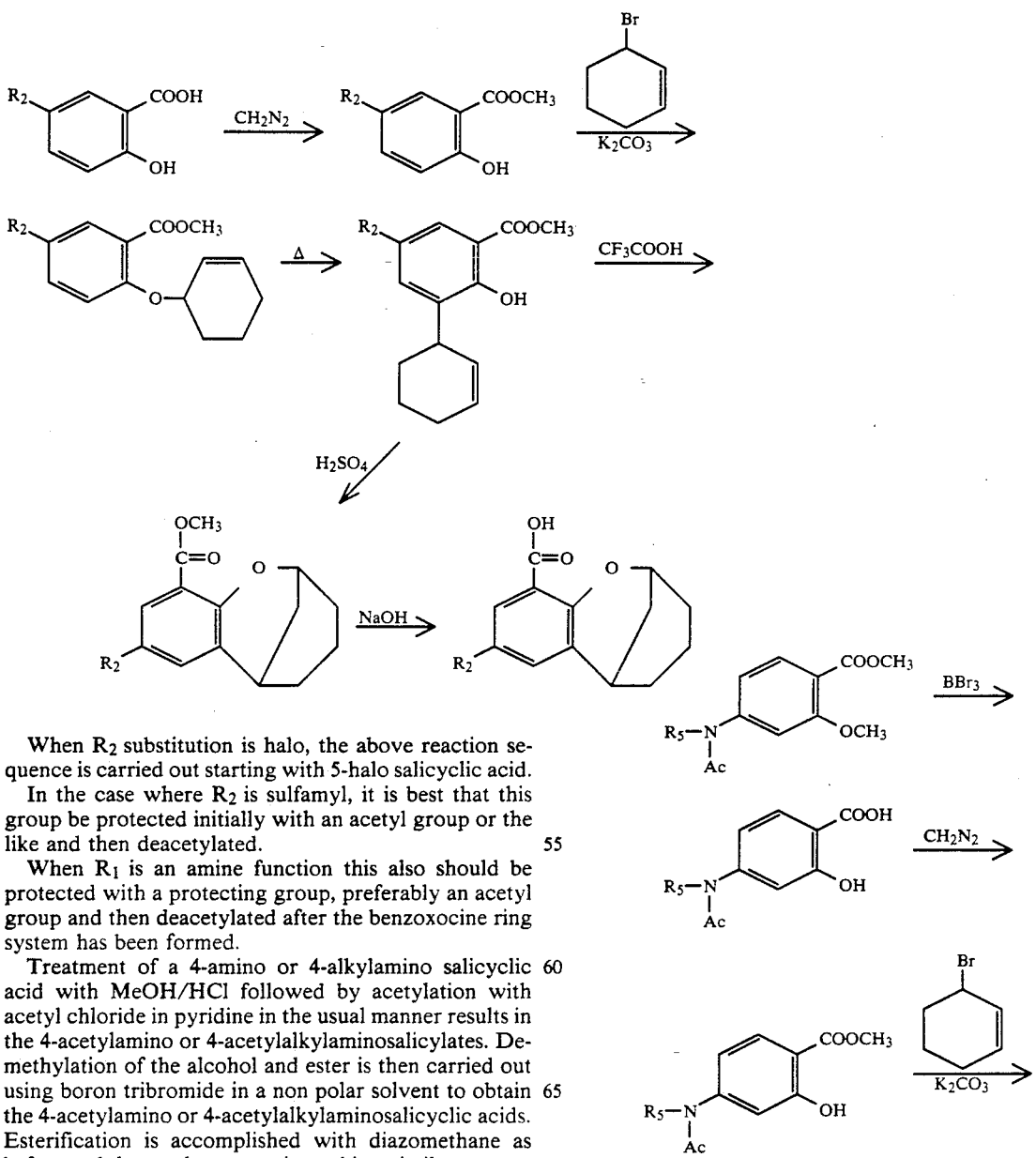

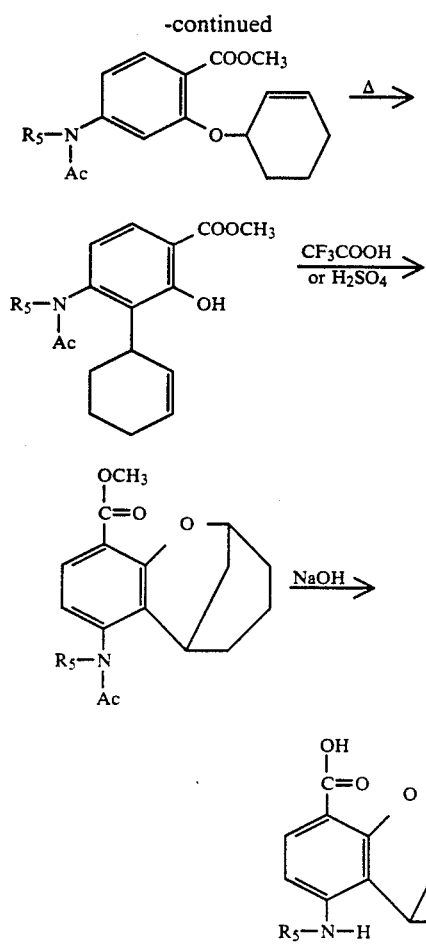

where R₅ is hydrogen or alkyl.

In a similar manner, when R₁ and R₂ are both substituted with groups other than hydrogen the following reaction sequences are possible.

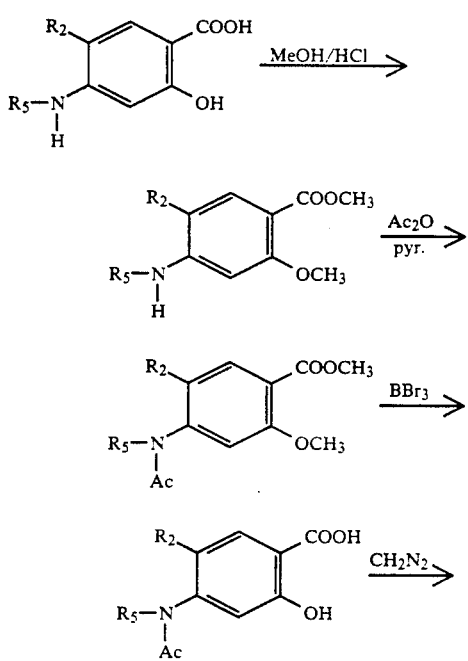

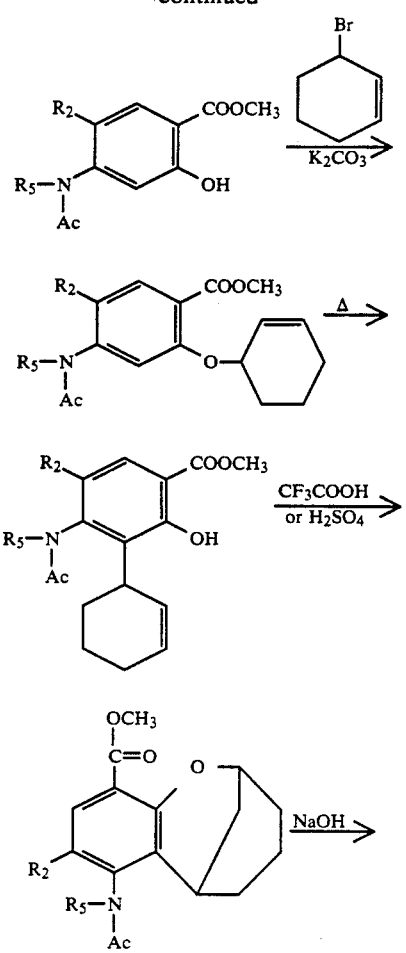

where R₅ is hydrogen or alkyl.

When it is desired to have R' or R″ substitution of alkyl then a suitable starting material should be used. Thus for example if the final product desired is 4-methyl-8-chloro-2,6-methano-2H-3,4,5,6-tetrahydro-1-benzoxocin-10-carboxylic acid then 3-bromo-5-methylcyclohexene should be used as reagent in place of 3-bromocyclohexene.

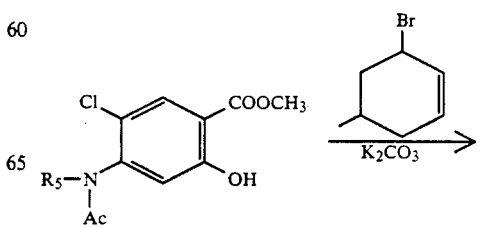

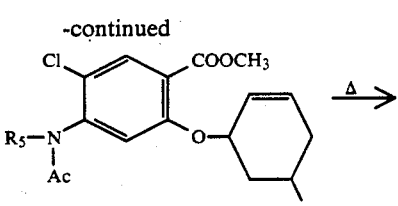

In a similar manner other compounds having R' or R" substitution are prepared.

When the benzoxocin-10-carboxylic acids are treated with N-chlorosuccinimide or N-bromosuccinimide in a polar medium (DMF) at room temperature, the resulting halogenated product is formed.

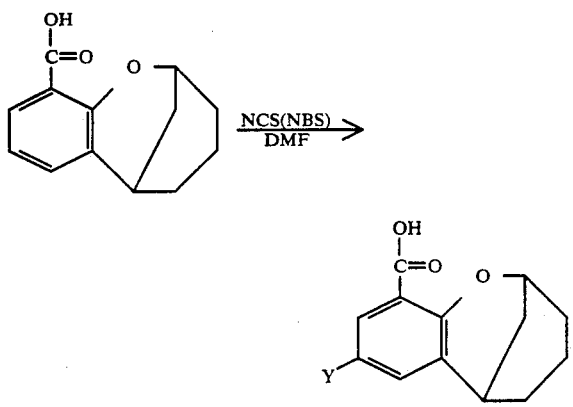

where Y is halo.

Halogenation may also be carried out on the 7-acetylamino compounds of the esters. Halogenation occurs in the 8-position. when these halogenated products are treated with base as above, hydrolysis gives the desired 7-amino-8-halo-10-carboxylic acids of this invention.

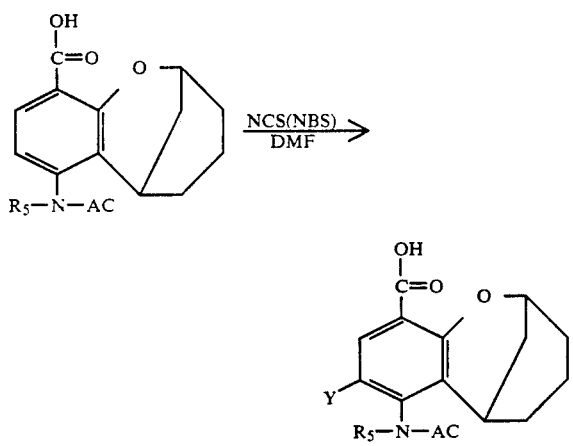

where Y is halo and $R_5$ is hydrogen or alkyl.

Certain compounds of this invention have at least one asymmetric carbon atom such as the 2,6-methano-2H-3,4,5,6-tetrahydro-1-benzoxocine or the corresponding dihydro compounds where at least one R, R' or R" is other than hydrogen and forms an asymmetric carbon atom or certain carbon atoms on the amido moiety. Further, certain compounds of this invention exist in their cis or trans configuration with respect to the 2 and 6 positions of the 2,6-methano-2H-3,4,5,6-tetrahydro-1-benzoxocine ring. As a result, those compounds of Formula I may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer, separated by conventional techniques such as chromatography or fractional crystallization from which each diastereomer is resolved. On the other hand, synthesis may be carried out by known stereospecific processes using the desired form of the intermediate which would result in obtaining the desired stereospecificity.

As a result, one can obtain the desired stereospecific compound. For example, and to illustrate the scope of this invention, one of the most preferred compounds of this invention is 10-[N-(1-azabicyclo[2.2.2]octan-3(S)-yl)carboxamido]-8-chloro-cis-2(S),6(R)-methano-2H-3,4,5,6-tetrahydro-1-benzoxocine. This has three asymmetric centers. These are at the 2 and 6 positions of the benzoxocine ring and at the 3 position of the quinuclidine moiety. Condensation of racemic 8-chloro-2,6-methano-2H-3,4,5,6-tetrahydro-1-benzoxocin-10-carboxylic acid and racemic 3-aminoquinuclidine as above results in the stereoisomeric mixture of 1 0-[N-(1-azabicyclo[2.2.2.]octan-3-yl)carboxamido]-8-chloro-2,6-methano-2H-3,4,5,6-tetrahydro-1-benzoxocine.

Such a mixture can exist as a single entity having its own chemical, physical and pharmacological properties and lies within the scope of the present invention. This mixture theoretically consists of eight individual stereoisomers having unique absolute configurations. Each of these stereoisomers also has its own chemical, physical and pharmacological properties and lies within the scope of this invention.

The stereoisomeric mixture can be divided into cis and trans configurations having their own specific properties and are also within the scope of this invention. The cis configuration for example, has four cis stereoisomers consisting of two racemates and four diastereoisomeric mixtures. The cis racemates and diastereoisomeric mixtures can also be considered to be separate entities because of their unique chemical, physical and pharmacological properties and are further included within the scope of this invention.

Resolution of such mixtures of the acids, esters or amides are carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

One can also obtain the desired stereospecific compound by reaction with resolved intermediates. For example, resolution of 3-aminoquinuclidine results in S-(−)-3-aminoquinuclidine and R-(+)-3-aminoquinuclidine. When S-(−)-3-aminoquinuclidine is reacted as above with the S,R configuration of 8-chloro-cis-2,6-methano-2H-3,4,5,6-tetrahydro-1-benzoxocin-10-carboxylic acid then the product prepared is 10-[N azabicyclo[2.2.2.]octan-3(S)-yl)carboxamido]-8-chloro-cis-2(S),6(R)methano-2H-3,4,5,6-tetrahydro-1-benzoxocine. In a similar manner the remaining various stereospecific compounds are prepared by reacting S-(−)-3-amino-quinuclidine or R-(+)-3-aminoquinuclidine with the cis (S,R) or cis (R,S) configuration or the trans (R,R) or trans (S,S) configuration of 8-chloro-2,6-methano-2H-3,4,5,6-tetrahydro-1-benzoxocin-10-carboxylic acid, acid halide or ester. The remaining compounds of Formula I are so prepared. Ring closure of methyl 3-(3-hexenyl)-5-chlorosalicylate results in predominantly cis formation.

The compounds of this invention may be readily converted to their nontoxic acid addition salts by customary methods in the art. The nontoxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, maleic acid, oxalic acid, succinic acid, glycolic acid, lactic acid, salicylic acid, benzoic acid, nicotinic acid, phthalic acid, stearic acid, oleic acid, abietic acid, etc.

We have found that compounds of this invention have gastric prokinetic and anti-emetic properties and lack $D_2$ receptor binding activity. As such they possess therapeutic value in the treatment of upper bowel motility and gastroesophageal reflux disorders. Further, compounds within the scope of this invention are useful in the treatment of disorders related to impaired gastrointestinal motility such as retarded gastric emptying, dyspepsia, flatulence, esophageal reflux, peptic ulcer and emesis. Further, compounds of this invention exhibit 5-$HT_3$ antagonism and are considered to be useful in the treatment of psychotic disorders such as schizophrenia and anxiety and in the prophylaxis treatment of migraine and cluster headaches. We have further found that certain compounds are selective in that they have little or no dopaminergic antagonist activity.

Various tests in animals can be carried out to show the ability of compounds of this invention to exhibit pharmacological responses that can be correlated with activity in humans. These tests involve such factors as the effect of the compounds of Formula I on gastric motility, emesis, selective antagonism of 5-$HT_3$ receptors and their $D_2$ dopamine receptor binding properties.

It has been found that compounds within the scope of this invention when tested in the above variety of situation show a marked activity.

One such test is the "Rat Gastric Emptying: Amberlite Bead Method". This test is carried out as follows:

The test is designed to assess the effects of a test agent on gastric emptying of amberlite beads in the rat. The procedure is a modification of those used in L. E. Borella and W. Lippman (1980) *Digestion* 20:26–49.

PROCEDURE

Amberlite ® beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N of 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite ® beads inteagastrically. The beads are delivered via a 3 inch piece of PE 205 tubing attached to a 16 gauge tubing adapter and syringe. A small piece of PE 50 tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining ion each stomach is counted after rinsing the beads with NaOH.

The number of beads remaining in each stomach is subtracted from 60 to obtain the number of beads emptied. The mean number of beads±S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance is determined using a t-test for independent samples with a probability of 0.05 or less considered to be significant.

In order to demonstrate the ability of compounds of this invention as antiemetic agents, the following test for "Cisplatin-Induced Emesis in the Ferret" may be used. This test is a modified version of paper reported by A. P. Florczyk, J. E. Schurig and W. T. Brodner in *Cancer Treatment Reports*: Vol. 66, No. 1. January 1982.

Cisplatin had been shown to cause emesis in the dog and cat. Florczyk, et al. have used the ferret to demonstrate the same effects.

PROCEDURE

Male castrated, Fitch ferrets, weighing between 1.0 and 1.5 kg have an indwelling catheter placed in the jugular vein. After a 2-3 day recovery period, the experimental procedure is begun. 30 minutes prior to administration of cisplatin, ferrets are dosed with the compound in 0.9% saline (i.v.) at a dose volume of 2.0 ml/kg. 45 minutes after administration of cisplatin, ferrets are again dosed with the 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to an fro movements. Concurrent with this behavior are several retching movements in a row, followed by a single, large, retch which may or may not expulse gastric contents. immediately following the single large retch, the ferret relaxes. Single coughs or retches are not counted as vomiting episodes.

5-HT$_3$ receptor binding may be assayed by the method of C. A. Milburn and S. J. Peroutka: *Mol. Pharmacol.* 16: 687–699, 1979.

D-2 Dopamine Receptor Binding Assay

The D-2 dopamine receptor binding assay has been developed with slight modifications using the method of Ian Cresse, Robert Schneider and Solomon H. Snyder, *Europ. J. Pharmacol.* 46: 377–381(1977). Spiroperidol is a butyrophenone neuroleptic whose affinity for dopamine receptors in brain tissue is greater than that of any other known drug. It is a highly specific D-1 dopamine (non-cyclase linked) receptor agent with K1 values of 0.1–0. for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleus (corpus striatum) is used as the receptor source because it contains the highest density of dopamine receptors in the brain and periphery.

PROCEDURE

Male Charles-River rats weighing 250–300 g are decapitated and their brains removed, cooled on ice, and caudate dissected immediately and frozen on dry ice. Tissue can be stored indefinitely at −70° C. For assay caudate is homogenized in 30 ml of tris buffer (pH 7.7 at 25° C.) using the polytron homogenizer. The homogenate is centrifuged at 40,000 g (18,000–19,000 RPM in SSp-34 rotor) for 15 minutes. Pellet is resuspended in fresh buffer and centrifuged again. The final pellet is resuspended in 150 volumes of assay buffer.

Specific 3H-spiroperidol binding is assayed in a total 2 ml reaction volume consisting of 500 μl of caudate homogenate, 50 mM tris buffer (pH 7.4 at 35° C.), 5 mM MgSO$_4$, 2 mM EDTA.2NA, 120 mM NaCl, 0.1% ascorbic acid, 0.4 nM $^3$H-spiroperidol and test compound or assay buffer. When catecholamines are included in the assay, 10 μM pargyline should be included in the reaction mixture to inhibit monoamine oxidase. Samples are incubated at 37° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 μM d(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248(1976) using Bio-Rad's coomassie blue G-250 dye reagent. Bovine gamma globulin supplied by BIO-RAD is used as the protein standard.

BEZOLD-JARISCH EFFECT IN ANAESTHETIZED RATS

Male rats 260–290 g are anaesthetized with urethane 1.25 g/kg$^{-1}$ i.p., and the trachea cannulated. The jugular vein is cannulated for intravenous (i.v.) injection of drugs. Blood pressure is recorded from a cannula in the left carotid artery and connected to a heparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rat, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injection of 5-HT. The effect of a compound on the 5-HT-evoked bradycardia is calculated as a percent of the bradycardia evoked by 5-HT before injection of compound.

In separate experiments to measure the duration of 5-HT antagonism caused by compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulse in 5 strains with a maximally effective voltage (20 V at 10 Hz). Pulse frequency may vary from 5–30 Hz and frequency-response curves are constructed before and 10 minutes after i.v. injection of a single dose of compound.

The results of these above tests indicate that compounds of this invention exhibit a valuable balance between the peripheral and central action of the nervous system and are useful in the treatment of disorders related to impaired gastro-intestinal motility such as gastric emptying, dyspepsia, flatulence, esophageal reflux and peptic ulcer and in the treatment of disorders of the central nervous system such as psychosis.

Compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsuled, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers and the like. Such compositions and preparations should contain at least 0.1% of active compound. The percentage of the compositions and preparations may, of course, be varies and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, genic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coating or to otherwise modify the physical form of the dosage unit. For instance, tablets, pills, or capsules may be coated with shellac, sugar or both. A syrup or elixir may contain the active compound. Sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example sugars or sodium chloride. Prolonged absorption of the injectable compositions of agent delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

Therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 50 mg/kg of body weight per day and higher although it may be administered in several different dosage units from once to several times a day. Higher dosages are required for oral administration.

The compounds of the present invention may be prepared by the following representative examples. The processes herein described are also representative of this invention and are not intended to be limiting in scope.

EXAMPLE 1

Methyl 5-chlorosalicylate

Thionyl chloride (900 g, 7.56 mol) is added dropwise to methanol (1977 g, 61.72 mol) at 20° C. over a period of 1.5 hours, maintaining the temperature between 15°–25° C. with an ice bath. The cooling bath is removed and 5-chlorosalicylic acid (1000 g, 5.8 mol) added in one portion, then slowly heated to reflux. On completion of the reaction the solution is cooled to $-5°$ C. for 1 hour. The methyl 5-chlorosalicylate is filtered, washed with cold methanol (150 ml) and dionized water (2×1 L). The solid is dried under house vacuum at 30° C. for 24 hours to give methyl 5-chlorosalicylate; m.p. 44°–46° C.

EXAMPLE 2

Methyl-5-chloro-2-(3'-cyclohexenyloxy)benzoate

A mixture of methyl-5-chlorosalicylate (5509, 2.95 mol), 3-bromocyclohexene (597.4 g, 3.71 mol), finely grounded potassium carbonate (815.0 g, 5.90 mol) and acetone (48609, 83.7 mol) are slowly heated to reflux and maintained at reflux for 24 hours. The mixture is cooled to 3040° C., the solids filtered, washed with acetone and the filtrate concentrated to dryness to give methyl-5-chloro-2-(3'-cyclohexenyloxy)benzoate as an oil which is used directly in the next step.

EXAMPLE 3

Methyl-5-chloro-3-(3'-cyclohexenyl)salicylate

A slurry of methyl-5-chloro-2-(3'-cyclohexenyloxy)-benzoate (603.6 g, 2.26 mol) and cesium carbonate (33.5 g, 0.1 mol) are heated, under a nitrogen blanket, to 155°-175° C. On completion of the reaction, the mixture is cooled to 80° C. and toluene (500 ml) added. The mixture is stirred for 1 hour and the solids removed by filtration. The filter cake is washed with toluene (2×65 ml) combined and concentrated to dryness to give an oil which is crystallized from denatured ethanol to obtain methyl-5-chloro-3-(3'-cyclohexenyl)salicylate; m.p. 59°-61° C.

EXAMPLE 4

Methyl 8-chloro-2,6-methano-2H-3,4,5,6-tetrahydro-1-benzoxocin-10-carboxylate

To concentrated sulfuric acid (519 ml) is added in portions methyl 5-chloro-3-(3'-cyclohexenyl)salicylate (345 g, 1.3 mol), keeping the temperature below 50° C. After stirring at room temperature for 1 hour the mixture is poured onto water (4.2 L), followed by neutralization with 50% aqueous sodium hydroxide (843 ml). This basic mixture is extracted with toluene (2.5 L), dried with sodium sulfate, filtered and evaporated to dryness to give methyl 8-chloro-2,6-methano-2H-3,4,5,6-tetrahydro-1-benzoxocin-10-carboxylate as an oil which is used directly in the next step.

EXAMPLE 5

8-Chloro-2,6-methano-2H-3,4,5,6-tetrahydro-1-benzoxocin-10-carboxylic acid

The ester, methyl 8-chloro-2,6-methano-2H-3,4,5,6-tetrahydro-1-benzoxocin-10-carboxylate (351.6 g) is added to a solution of lithium hydroxide, monohydrate (131.0 g, 3.12 mol) in water (2.6 L) and the mixture heated to reflux for 1.5 hours. This results in the formation of a heavy precipitate. The reaction mixture is cooled to room temperature, ethyl acetate (1.7 L) is added followed by acidification with concentrated hydrochloric acid (276 ml). The ethyl acetate is removed and the acidic aqueous layer further extracted with ethyl acetate (500 ml). The ethyl acetate extracts are combined, dried with sodium sulfate, filtered and evaporated to dryness to give 8-chloro-2,6-methano-2H-3,4,5,6-tetrahydro-1-benzoxocin-10-carboxylic acid as an off-white solid. Recrystallization from acetonitrile gives pure product; m.p. 110°-120° C.

EXAMPLE 6

8-Chloro-2(S),6(R)-methano-2H-3,4,5,6-tetrahydro-1-benzoxocin-10-carboxylic acid 8-Chloro-2(R),6(S)-methano-2H-3,4,5,6-tetrahydro-1-benzoxocin-10-carboxylic acid (S)-4-nitro-α-methylbenzylamine hydrochloride (139.39, 9.69 mol) is added to 50% aqueous sodium hydroxide (59 ml) and the mixture extracted with methylene chloride (2×700 ml). The methylene chloride is separated, dried with sodium sulfate, filtered and evaporated to dryness to give the free base as an oil, which is dissolved in methanol (1 L).

The racemic acid 8-chloro-2,6-methano-2H-3,4,5,6-tetrahydro-1-benzoxocin-10-carboxylic acid (173.79, 0.69 mol) is added to the above methanolic solution and stirred to give a homogeneous solution. Within 0.5 hours a white precipitate forms. The solvent is removed under reduced pressure and the crude salt mixture suspended in ethyl acetate (700 ml) and methanol (500 ml) and heated to reflux to give a clear solution. On cooling to room temperature the solids are filtered and washed with ethyl acetate. The solids are recrystallized from refluxing ethyl acetate/methanol (400 ml/250 ml) to give the resolved salt. This is then partioned between methylene chloride (400 ml) and aqueous 1N hydrochloric acid. The layers are separated and the aqueous layer re-extracted with methylene chloride (200 ml). The combined organic layers are dried with sodium sulfate, filtered and concentrated to dryness to give an oil, which, on trituration with ether gives the resolved acid 8-chloro-2(S),6(R)-methano-2H-3,4,5,6-tetrahydro-1-benzoxocin-10-carboxylic acid; m.p. 114°-119° C.

When the above resolution is followed and (R)-4-nitro-α-methylbenzylamine hydrochloride is substituted for (S)-4-nitro-α-methylbenzylamine hydrochloride then the product prepared is 8-chloro-2(R),6(S)-methano-2H-3,4,5,6-tetrahydro-1-benzoxocin-10-carboxylic acid.

EXAMPLE 7

10-[N-(1-azabicyclo[2.2.2.]octan-3(S)-yl)carboxamido]-8-chloro-2(S),6(R)-methano-2H-3,4,5,6-tetrahydro-1-benzoxocine 10-[N-(1-azabicyclo[2.2.2.]octan-3(S)-yl)carboxamido]-8-chloro-2(R),6(S)-methano-2H-3,4,5,6-tetrahydro-1-benzoxocine The (S,R) acid 8-chloro-2(S),6(R)-methano-2H-3,4,5,6-tetrahydro-1-benzoxocin-10-carboxylic acid (5.09 g, 0.02 mol) is dissolved in chloroform (90 ml) and heated to 35° C. under nitrogen. A solution of thionyl chloride (3.0 g, 0.025 mol) in chloroform (10 ml) is added over 15 minutes between 40° and 45° C. The reaction is allowed to stir at 40°-45° C. for 4 hours at which time TLC (Hexane:EtOH 9:1) shows the reaction to be complete. The reaction mixture is evaporated to dryness by means of azeotroping with toluene, to give the acid chloride as an oil which is dissolved in toluene (2 ml). (S)-3-aminoquinuclidine dihydrochloride (5 g, 0.025 mol) is dissolved in a solution of 50% aqueous sodium hydroxide (4.1 g) and methanol (20 ml) and stirred for 5 minutes. The mixture is filtered and the filtrate evaporated to dryness to give a semi-solid. This is treated with toluene and stirred at 50° C. for 5 minutes, filtered, and the filtrate evaporated to dryness. The residue is dissolved in toluene (60 ml) and the previously prepared acid chloride added over 30 minutes dropwise to the 3-aminoquinuclidine free base keeping the temperature between 40°-45° C. The reaction mixture is stirred at 40° C. for 4 hours, cooled to room temperature and a solution of 50% aqueous sodium hydroxide (1.69) in water (80 ml) added. The mixture is stirred for 5 minutes, the toluene layer removed, washed with water, dried over sodium sulfate, filtered and evaporated to dryness to give 10-[N-(1-azabicyclo[2.2.2.]octan-3(S)-yl)carboxamido]-8-chloro-2(S),6(R)-methano-2H-3,4,5,6-tetrahydro-1-benzoxocine as a glassy solid; m.p. 115° C.

|   | Calc'd | Found |
| --- | --- | --- |
| C | 66.6 | 66.81 |
| H | 6.98 | 7.11 |

| | Calc'd | Found |
|---|---|---|
| N | 7.76 | 8.01 |

When 8-chloro-2(R),6(S)-methano-2H-3,4,5,6-tetrahydro-1-benzoxocin-10-carboxylic acid is used with (S)-3-aminoquinuclidine then the product prepared is 10-[N-(1-azabicyclo[2.2.2.]octan-3(S)-yl)carboxamido]-8-chloro-2(R),6(S)-methano-2H-3,4,5,6-tetrahydro-1-benzoxocine.

When (R)-3-aminoquinuclidine is used in the above examples then the corresponding products are obtained.

EXAMPLE 8

10-[N-(1-azabicyclo[2.2.2.]octan-3-yl)carboxamido]-8-chloro-2,6-methano-2H-3,4,5,6-tetrahydro-1-benzoxocine To a cold solution of 8-chloro-2,6-methano-2H-3,4,5,6-tetrahydro-1-benzoxocin-10-carboxylic acid (1.36 g) in 40 ml of chloroform is added triethylamine (0.8 g) at room temperature. To this is added of ethylchloroformate (0.7 g) in chloroform (10 ml) and stirring continued for 1.5 hours. This is added in one portion to a mixture of $K_2CO_3$ (15 g) in water (25 ml) containing 3-aminoquinuclidine dihydrochloride (5 g). Stirring is continued overnight. The reaction mixture is diluted with chloroform (100 ml) and the organic layer separated, washed twice with water, dried over magnesium sulfate and evaporated to dryness to give crude product which is purified by flash chromatography using 10% methanol/chloroform to give 10-[N-(1-azabicyclo[2.2.2.]octan-3-yl)carboxamido]-8-chloro-2,6-methano-2H-3,4,5,6-tetrahydro-1-benzoxocine.

EXAMPLE 9

When 5-chlorosalicylic acid is replaced in Example 1 with salicylic acid, 5-bromosalicylic acid or 5-methylsulfonylsalicylic acid then the products prepared following the procedures of Examples 1–8 are 10-[N-(1-azabicyclo[2.2.2.]octan-3-yl)carboxamido]-2,6-methano-2H-3,4,5,6-tetrahydro-1-benzoxocine; 10-[N-(1-azabicyclo[2.2.2.]octan-3-yl)carboxamido]-8-bromo-2,6-methano-2H-3,4,5,6-tetrahydro-1-benzoxocine and 10-[N-(1-azabicyclo[2.2.2.]octan-3-yl)carboxamido]-8-methylsulfamyl-2,6-methano-2H-3,4,5,6-tetrahydro-1-benzoxocine.

EXAMPLE 10

Methyl 7-acetylamino-8-chloro-2,6-methano-2H-3,4,5,6-tetrahydro-1-benzoxocin-10-carboxylate A mixture of methyl 3-(3'-cyclohexenyl)-4-acetylamino-5-chlorosalicylate (1.2 g) and trifluoroacetic acid (5 mL) are stirred at room temperature overnight. The acid is removed under vacuum and the residue diluted with ether, washed with sodium bicarbonate, then water, dried and evaporated to dryness to give crude methyl 7-acetylamino-8-chloro-2,6-methano-2H-3,4,5,6-tetrahydro-1-benzoxocin-10-carboxylate. This product is purified by flash chromatography using 10% ethyl acetate/hexane to give pure product.

EXAMPLE 11

7-Amino-8-chloro-2,6-methano-2H-3,4,5,6-tetrahydro-1-benzoxocin-10-carboxylic acid To a solution of sodium (0.3 g) in methanol (15 mL is added methyl 7-acetylamino-8-chloro-2,6-methano-2H-3,4,5,6-tetrahydro-1-benzoxocin-10-carboxylate (0.6 g). Stirring is continued at 60° C. for two days. This is then diluted with 1N sodium hydroxide (5 mL) and stirring continued at 60° C. overnight. The methanol is removed in vacuum, diluted with water, filtered, acidified with acetic acid, filtered, extracted with ethyl acetate, washed with water, dried over magnesium sulfate and evaporated to dryness to obtain 7-amino-8-chloro-2,6-methano-2H-3,4,5,6-tetrahydro-1-benzoxocin-10-carboxylic acid. This is purified by crystallization from ethyl acetate/ether.

EXAMPLE 12

10-[N-(1-azabicyclo[2.2.2.]octan-3-yl)carboxamido]-7-amino-8-chloro-2,6-methano-2H-3,4,5,6-tetrahydro-1-benzoxocine To a cold solution of 7-amino-8-chloro-2,6-methano-2H-3,4,5,6-tetrahydro-1-benzoxocin-10-carboxylic acid (0.3 g) in chloroform (40 mL) is added triethylamine (0.3 g) and then ethylchloroformate (0.2 g) in chloroform (10 mL). Stirring is continued for 2 hours. This is then added to a cold mixture of 3-aminoquinuclidine dihydrochloride (3 g) in water (20 ml) containing $K_2CO_3$ (7.5 g). Stirring is continued overnight. The reaction mixture is then diluted with chloroform, the two layers separated and the chloroform layer washed twice with water, dried over magnesium sulfate, filtered and evaporated to dryness to give 10-[N-(1-azabicyclo[2.2.2.]octan-3-yl)carboxamido]-7-amino-8-chloro-2,6-methano-2H-3,4,5,6-tetrahydro-1-benzoxocine.

EXAMPLE 13

When 3-(3-cyclohexyl)-4-acetylamino-5-chlorosalicylate in Example 10 is replaced with 3-(3'-cyclohexyl)-4-acetylaminosalicylate; 3(3'-cyclohexyl)-4-methylamino-5-chlorosalicylate; 3-(3'-cyclohexyl)-5-sulfanylsalicylate or 3-(3'-cyclohexyl)-5-methylsulfamylsalicylate and the procedures of Examples 10-12 are followed then the products prepared are respectively 10-[N-(1-azabicyclo[2.2.2.]octan-3-y-l)carboxamido]-7amino-2,6-methano-2H-3,4,5,6-tetrahydro-1-benzoxocine; 10-[N-(1-azabicyclo-[2.2.2.]octan-3-yl)carboxamido]-7-methylamino-8-chloro-2,6-methano-2H-3,4,5,6-tetrahydro-1-benzoxocine; 10-[N-(1-azabicyclo[2.2.2.]octan-3-yl)carboxamido]-8-sulfamyl-2,6-methano-2H-3,4,5,6-tetrahydro-1-benzoxocine and 10-[N-(1-azabicyclo[2.2.2.]octan-3yl)carboxamido]-8-methylsulfamyl-2,6-methano-2H-3,4,5,6-tetrahydro-1-benzoxocine.

EXAMPLE 14

When 3-aminoquinuclidine dihydrochloride in Examples 7, 8, 9, 12 and 13 is replaced by the amines of Table I below, then the corresponding representative carboxamides of Table II below are prepared.

TABLE I

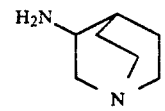

TABLE I-continued 3-aminoquinuclidine which is 3-amino-1-azabicyclo[2.2.2.]octane

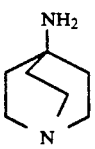

4-amino-1-azabicyclo[2.2.2.]octane

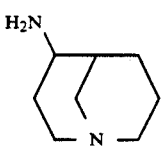

4-amino-1-azabicyclo[3.3.1.]nonane

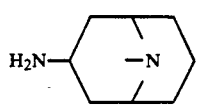

3-amino-9-methyl-9-azabicyclo[3.3.1.]nonane

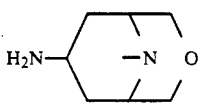

3-amino-7-oxo-9-methyl-9-azabicyclo[3.3.1.]nonane

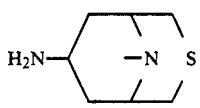

3-amino-7-thia-9-methyl-9-azabicyclo[3.3.1.]nonane

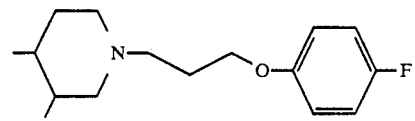

1-(p-fluorophenoxypropyl)-3-methoxy-4-aminopiperidine

TABLE II

10-[N-(1-azabicyclo[3.3.1.]non-4-yl)carboxamido]-8-chloro-2,6-methano-2H-3,4,5,6-tetrahydro-1-benzoxocine 10-[N-(1-azabicyclo[2.2.2.]oct-4-yl)carboxamido]-8-chloro-2,6-methano-2H-3,4,5,6-tetrahydro-1-benzoxocine 10-[N-(9-methyl-9-azabicyclo[3.3.1.]non-3-yl)carboxamido]-8-chloro-2,6-methano-2H-3, 4,5,6-tetrahydro-1-benzoxocine 10-[N-(7-oxo-9-methyl-9azabicyclo[3.3.1.]non-3-yl)carboxamido]-8-chloro-2,6-methano-2H,3,4,5,6-tetrahydro-1-benzoxocine 10-[N-(1-(p-fluorophenoxypropyl)-3-methxoypiperidin-4-yl)carboxamido]8-chloro-2,6-methano-2H-3,4,5,6-tetrahydro-1-benzoxocine 10-[N-(1-azabicyclo[3.3.1.]non-4-yl)carboxamido]-7-amino-8-chloro-2,6-methano-2H,3,4,5,6-tetrahydro-1-benzoxocine 10-[N-(1-azabicyclo[2.2.2.]oct-4-yl)carboxamido]-7-amino-8-chloro-2,6-methano-2H-3,4,5,6-tetrahydro-1-benzoxocine 10-[N-(9-methyl-9-azabicyclo[3.3.1.]non-3-yl)carboxamido]-7-amino-8-chloro-2,6-methano-2H,3,4,5,6-tetrahydro-1-benzoxocine 10-[N-(9-methyl-7-thia-9-azabicyclo[3.3.1.]non-3-yl)carboxamido-8-chloro-2,6-methano-2H-3,4.5,6-tetrahydro-1-benzoxocine 10-[N-(9-methyl-7-oxo-9-azabicyclo[3.3.1.]non-3-yl)carboxamido]-

TABLE II-continued 8-chloro-2,6-methano-2H-3,4,5,6-tetrahydro-1-benzoxocine

10-[N-(7-oxo-9-methyl-9-azabicyclo[3.3.1.]non-3-yl)carboxamido]-7-amino-8-chloro-2,6-methano-2H-3,4,5,6-tetrahydro-1-benzoxocine 10-[N-(1-(p-fluorophenoxypropyl)-3-methoxypiperidin-4-yl)carboxamido]-7-amino-8-chloro-2,6-methano-2H-3,4,5,6-tetrahydro-1-benzoxocine

EXAMPLE 15

When 3-bromocyclohexane of Example 2 is replaced by 3-bromo-4-methylcyclohexene; 3-bromo-5-methyl-cyclohexene or 3-bromo-6-methylcyclohexene, then the corresponding products are prepared following Examples 2–14.

EXAMPLE 16

Methyl 7-acetylamino-8-chloro-2,6-methano-2,3,4,5-tetrahydro-1-benzoxocine

Methyl 7-acetylamino-8-chloro-2,6-methane-2H-3,4-dihydro-1-benzoxocine

A mixture of methyl 7-acetylamino-8-chloro-2,6-methano-2H-3,4,5,6-tetrahydro-1-benzoxocin-10-carboxylate (1 g) and dichlorodicyanobenzoquinone (1 g) in benzene (15 mL) is stirred and heated at 80° C. in a sealed tube for 8 hours. The cooled reaction mixture is then diluted with benzene, filtered and evaporated to dryness. Purification by flash chromatography gives methyl 7-acetylamino-8-chloro-2,6-methano2,3,4,5-tetrahydro-1-benzoxocine and methyl 7-acetylamino-8-chloro-2,6-methano-2H-3,4-dihydro-1-benzoxocine.

EXAMPLE 17

10-[N-(1-azabicyclo[2,2,2,]octan-3-yl)carboxamido]-7-amino-8-chloro-2,6-methano-2,3,4,5-tetrahydro-1-benzoxocine 10-[N-(1-azabicyclo[2,2,2,]octan-3-yl)carboxamido]-7-amino-8-chloro-2,6-methano-2H-3,4-dihydro-1-benzoxocine When the procedure of Examples 11 and 12 are followed, however, methyl 7-acetylamino-8-chloro-2,6-methano-2H-3,4,5,6-tetrahydro-1-benzoxocin-10-carboxylate is replaced by methyl 7-acetylamino-8-chloro-2,6-methano-2,3,4,5-tetrahydro-1-benzoxocine or methyl 7-acetylamino-8-chloro-2,6-methano-2H-3,4-dihydro-1-benzoxocine then the captioned products are prepared.

The following is taken from Example 24 of U.S. Pat. No. 4,863,921 and Application Ser. No. PCT/US89/01739.

Methyl 2-chloro-cis-5I,6,7,8,9,9a-hexahydrodibenzofuran-4-carboxylate

Methyl 2-chloro-trans-5a,6,7,8,9,9a-hexahydrodibenzofuran-4-carboxylate

A mixture of 9 g of methyl 3-(3-cyclohexenyl)-5-chlorosalicylate and 20 ml trifluoroacetic acid is heated at 70° C. overnight. The cooled reaction mixture is diluted with hexanes, washed three times with water, dried and evaporated to dryness. The residue is purified with flash chromatography using 10% ethyl acetate/hexane to give four fractions. First fraction 2.29 of material (mixture of at least two materials); second fraction 2.29 cis isomer; third fraction 1.69 mixture of cis and trans isomers; and fourth fraction 19 trans isomer.

Based on X-ray crystallographic data the fourth fraction is methyl 8-chloro-cis-2,6-methano-2H-3,4,5,6-tetrahydro-1-benzoxocin-10-carboxylate.

The following is taken from Example 26 of U.S. Pat. No. 4,863,921 and application Ser. No. PCT/US89/01739.

Following the procedure of Example 25 but using the trans isomer in place of the cis, the corresponding 2-chloro-trans-5a,6,7,8,9,9a-hexahydrodibenzofuran-4-carboxylic acid is prepared.

Based on X-ray data the product prepared in Example 25 is 8-chloro-cis-2,6-methano-2H-3,4,5,6-tetrahydro-1-benzoxocin-10-carboxylic acid.

The following is taken from Example 27 of U.S. Pat. No. 4,863,921 and application Ser. No. PCT/US89/01739.

2-Chloro-cis-5a,6,7,8,9,9a-hexahydrodibenzofuran-4-(N-1-azabicyclo[2.2.2.]oct-3-yl)carboxamide 2-Chloro-trans-5a,6,7,8,9,9a-hexahydrodibenzofuran-4-(N-1-azabicyclo[2.2.2.]oct-3-yl)carboxamide Following the procedures of Examples 6 and 16 but substituting the cis and trans isomers of Examples 25 and 26, then the above captioned products are prepared.

Based on the X-ray data for the acid starting material prepared in Example 26, the product prepared in Example 27 is 10-[N-(1-azabicyclo[2.2.2.]octan-3-yl)carboxamido]-8-chloro-cis-2,6-methano-2H-3,4,5,6-tetrahydro-1-benzoxocine.

The following is taken from Example 36 of U.S. Pat. No. 4,863,921 and application Ser. No. PCT/US89/01739.

When the procedures of Examples 34 and 35 are followed but using 2-chloro-trans-5a, 6,7,8,9,9a-hexahydrodibenzo-furan-4carboxylic acid from Example 26 then the corresponding 2-chloro-trans-5aS,6,7,8,9,9aR-hexahydro-dibenzofuran-4-carboxylic acid and 2-chloro-trans-5aR,6,7,8,9aS-hexahydrodibenzofuran-4-carboxylic acid are prepared.

Based on X-ray crystallographic data from the acid starting material prepared in Example 26, the starting material to be resolved in Example 36 is 8-chloro-cis-2,6-methano-2H-3,4,5,6-tetrahydro-1-benzoxocin-10-carboxylic acid and the materials resolved are be 8-chloro-cis-2(R),6(S)-methano-2H3,4,5,6-tetrahydro-1-benzoxocin-10-carboxylic acid and 8-chloro-cis-2(S),6(R)-methano-2H-3,4,5,6-tetahydro-1-benzoxocin-10-carboxylic acid.

We claim:

1. A product prepared by the treatment of a compound of the formula

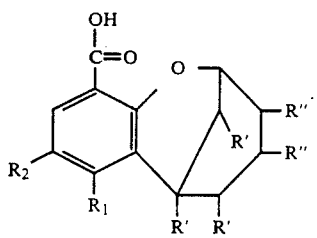

and its steroisomers, enantiomers, diasteroisomers and racemic mixtures with an amine of the formula H$_2$N-Z; where:

R$_1$ is hydrogen, an amino or alkylamino optionally substituted with a protecting group halo or haloalkyl;

R$_2$ is hydrogen, halo, sulfamyl, mono- and di-alkylsulfamyl or haloalkyl;

R' and R" are hydrogen or alkyl; and

Z is:

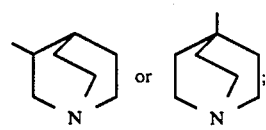

and its racemic mixtures and stereospecific isomers.

2. A product according to claim 1 of the formula

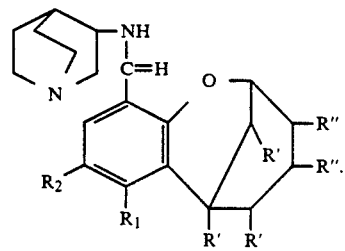

3. A product according to claim 2 which further includes removal of the protecting group on R$_1$ to form an amino or alkylamino.

4. A product according to claim 3 where R$_2$ is chloro, R$_1$ is amino and R' and R" are hydrogen.

5. A product according to claim 2 where R$_2$ is chloro and R$_1$, R' and R" are hydrogen.

6. A compound of the formula:

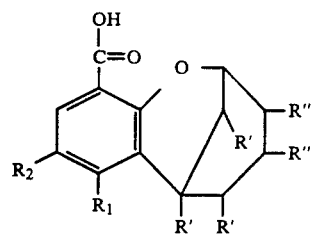

where:

R is NH-Z;

R$_1$ is hydrogen, an amino or alkylamino optionally substituted with a protecting group, halo or haloalkyl;

R$_2$ is hydrogen, halo, sulfamyl, mono- and di-alkylsulfamyl optionally substituted with a protecting group or haloalkyl;

R' and R" are hydrogen or alkyl;

vicinal R' and/or R" groups may form a C=C double bond; and

Z is

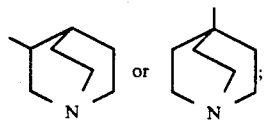

and its stereoisomers, enantiomers, diastereoisomers and racemic mixtures; or pharmaceutically acceptable salts thereof.

7. A compound according to claim 6 where:

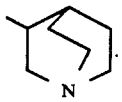

Z is

8. A compound according to claim 7 which is 10-[N-(1-azabicyclo[2.2.2.]-octan-3-yl)carboxamido-8-chloro-cis-2,6-methano-2H-3,4,5,6-tetrahydro-1-benzoxocine.

9. A compound according to claim 7 which is 10-[N-(1-azabicyclo[2.2.2.]-octan-3(S)-yl)carboxamido]-8-chloro-2(S),6(R)-methano-2H-3,4,5,6-tetrahydro-1-benzoxocine.

10. A compound according to claim 7 which is 10-[N-(1-azabicyclo[2.2.2.]-octan-3(S)-yl)carboxamido]-8-chloro-2(R),6(S)-methano-2H-3,4,5,6-tetrahydro-1-benzoxocine.

11. A method for the treatment of gastric disorders in humans and mammals suffering from such disorders comprising administering thereto an effective amount of a compound of claim 6.

12. A method for the treatment of emesis in humans and mammals in need of such treatment comprising administering thereto an effective amount of a compound of claim 6.

13. A pharmaceutical composition for the treatment of gastric disorders and/or emesis in humans and mammals wherein the active ingredient is an effective amount of a compound of claim 6 in admixture with a pharmaceutical carrier.

14. A method for the treatment of gastric disorders in humans and mammals suffering from such disorders comprising administering thereto an effective amount of a compound of claim 7.

15. A method for the treatment of emesis in humans and mammals in need of such treatment comprising administering thereto an effective amount of a compound of claim 7.

16. A pharmaceutical composition for the treatment of gastric disorders and/or emesis in humans and mammals wherein the active ingredient is an effective amount of a compound of claim 7 in admixture with a pharmaceutical carrier.

* * * * *